(12) United States Patent
Flury et al.

(10) Patent No.: US 11,559,324 B2
(45) Date of Patent: Jan. 24, 2023

(54) ATHERECTOMY SYSTEM WITH SUPPLY LINE FITMENT

(71) Applicant: BOSTON SCIENTIFIC LIMITED, Hamilton (BM)

(72) Inventors: Kristi Mae Flury, Maple Grove, MN (US); Sharath Badadamath, Hosapete (IN); Laszlo Trent Farago, Hudson, WI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 373 days.

(21) Appl. No.: 16/744,126

(22) Filed: Jan. 15, 2020

(65) Prior Publication Data
US 2020/0222075 A1 Jul. 16, 2020

Related U.S. Application Data

(60) Provisional application No. 62/792,808, filed on Jan. 15, 2019.

(51) Int. Cl.
*A61B 17/3207* (2006.01)
*A61B 17/00* (2006.01)

(52) U.S. Cl.
CPC .......... *A61B 17/320758* (2013.01); *A61B 2017/0042* (2013.01); *A61B 2017/00398* (2013.01); *A61B 2017/00973* (2013.01); *A61B 2217/005* (2013.01); *A61B 2217/007* (2013.01)

(58) Field of Classification Search
CPC .. A61B 17/320758; A61B 2017/00398; A61B 2017/0042; A61B 2017/00973; A61B 2217/005; A61B 2217/007
See application file for complete search history.

(56) References Cited

U.S. PATENT DOCUMENTS

| 5,827,323 | A | 10/1998 | Klieman et al. |
| 9,931,488 | B2 | 4/2018 | Bunch et al. |
| 2004/0068270 | A1 | 4/2004 | Allred, III |
| 2009/0124975 | A1 | 5/2009 | Oliver et al. |
| 2011/0213391 | A1 | 9/2011 | Rivers et al. |

(Continued)

FOREIGN PATENT DOCUMENTS

| EP | 2011446 A2 | 7/2009 |
| JP | H0295359 A | 4/1990 |

(Continued)

OTHER PUBLICATIONS

International Search Report and Written Opinion dated Apr. 22, 2020 for International Application No. PCT/US2020/013764.

*Primary Examiner* — Ashley L Fishback
(74) *Attorney, Agent, or Firm* — Seager, Tufte & Wickhem LLP

(57) ABSTRACT

An atherectomy system includes a handle having a handle housing and a drive motor that is disposed within the handle housing and is adapted to rotate a drive cable extending through the handle and operably coupled to an atherectomy burr. A supply line extends from the handle housing. A supply line fitment may be disposed relative to the handle housing and may be configured to releasably secure the supply line relative to the handle housing such that the supply line is directed away from the handle housing in a direction that is selected from two or more directions.

20 Claims, 7 Drawing Sheets

(56) References Cited

U.S. PATENT DOCUMENTS

| | | | |
|---|---|---|---|
| 2016/0235441 A1* | 8/2016 | Parkin | A61B 17/3468 |
| 2017/0296200 A1 | 10/2017 | Singer et al. | |
| 2017/0299101 A1 | 10/2017 | Singer et al. | |
| 2018/0183179 A1 | 6/2018 | Byrd et al. | |

FOREIGN PATENT DOCUMENTS

| | | |
|---|---|---|
| JP | H05305096 A | 11/1993 |
| JP | H10174689 A | 6/1998 |
| JP | 2004508875 A | 3/2004 |
| JP | 2014138846 A | 7/2014 |
| JP | 2016052587 A | 4/2016 |
| JP | 2019519259 A | 7/2019 |
| WO | 9814124 A1 | 4/1998 |
| WO | 0224089 A1 | 3/2002 |
| WO | 2011060192 A1 | 5/2011 |
| WO | 2017180717 A1 | 10/2017 |

\* cited by examiner

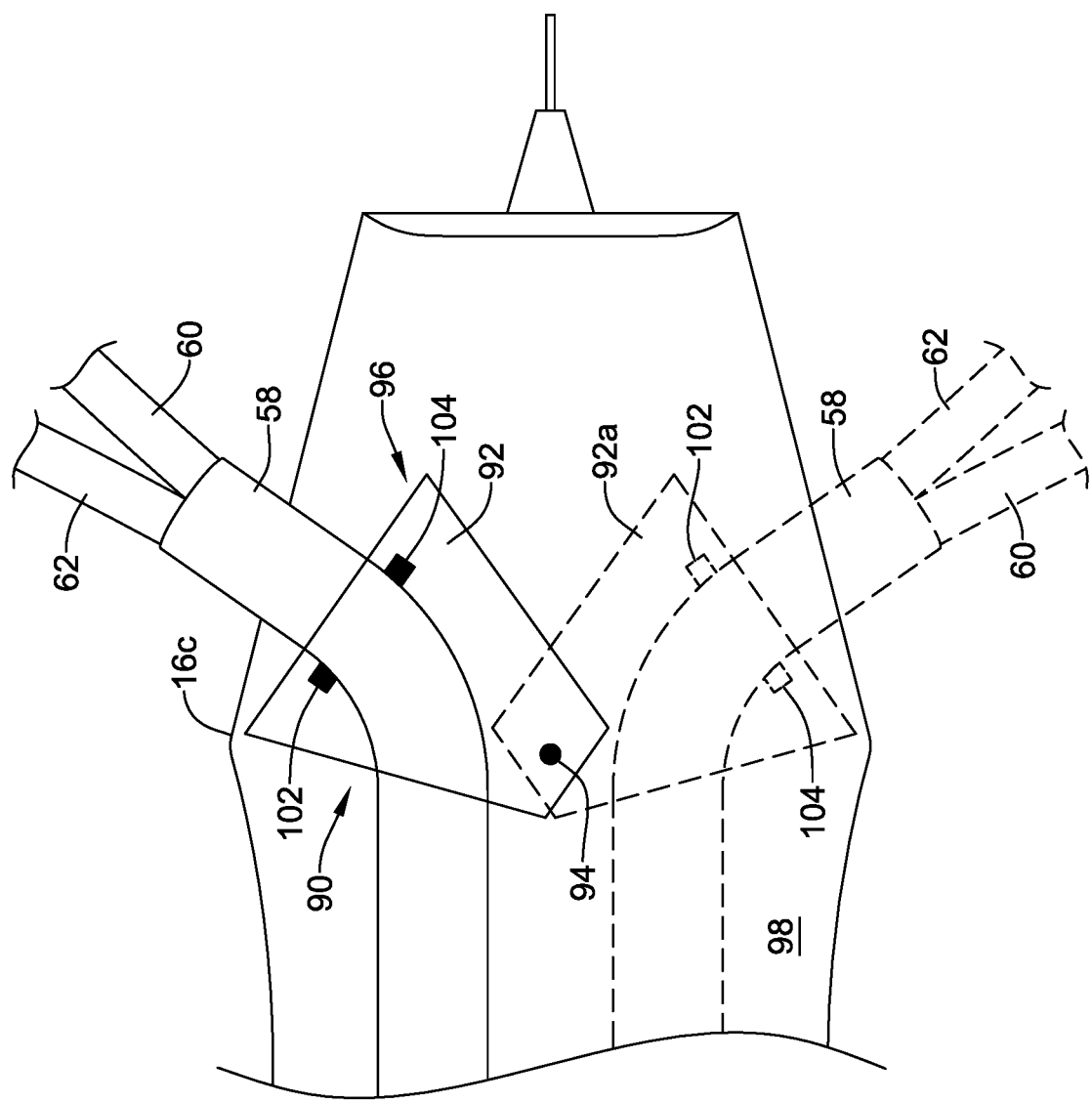

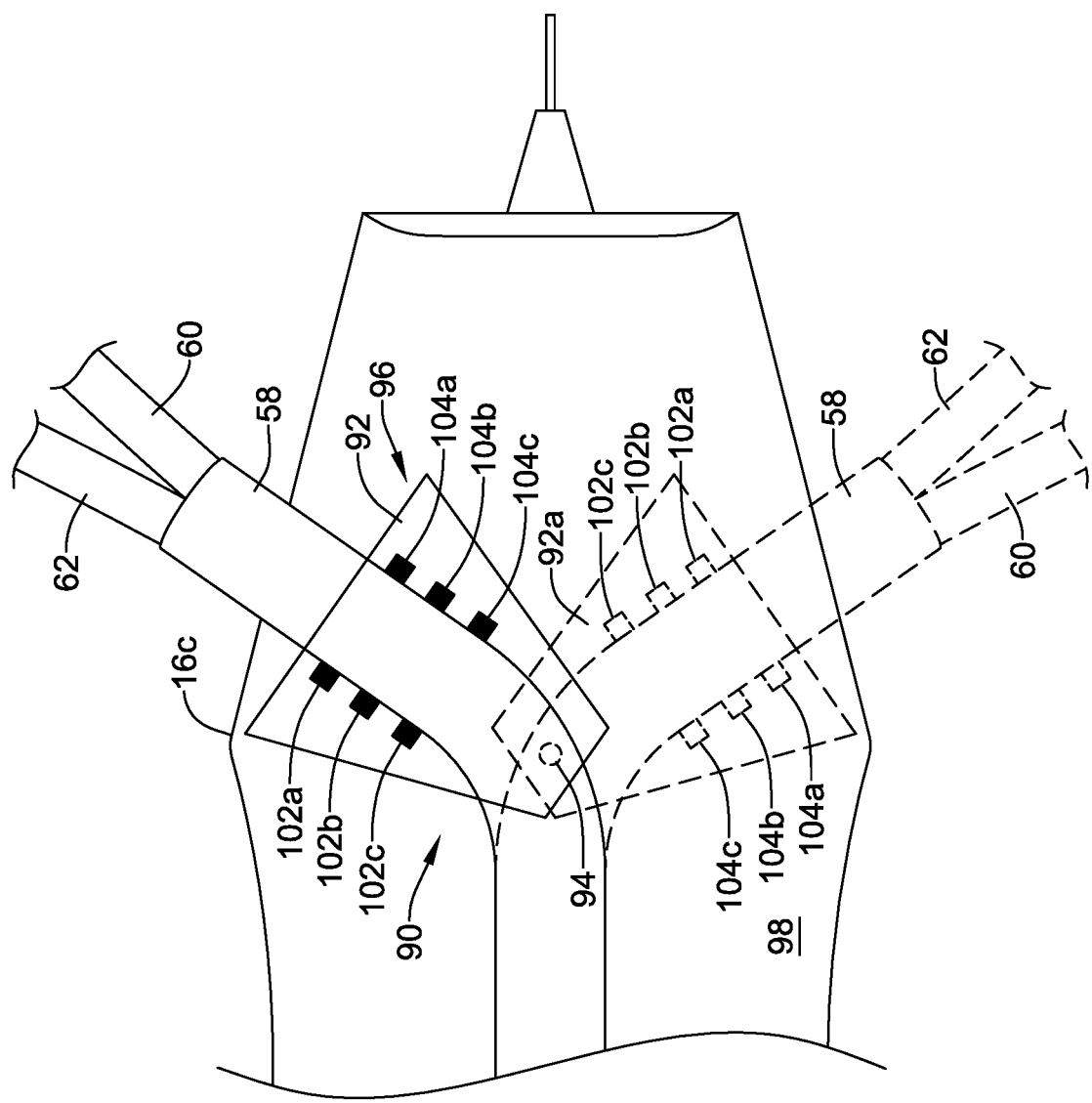

ATHERECTOMY SYSTEM WITH SUPPLY LINE FITMENT

CROSS-REFERENCE TO RELATED APPLICATIONS

This application claims the benefit of priority under 35 U.S.C. § 119 to U.S. Provisional Application Ser. No. 62/792,808, filed Jan. 15, 2019, the entirety of which is incorporated herein by reference.

TECHNICAL FIELD

The present disclosure pertains to medical devices, and methods for manufacturing and using medical devices. More particularly, the disclosure is directed to devices and methods for removing occlusive material from a body lumen. Further, the disclosure is directed to an atherectomy device for forming a passageway through an occlusion of a body lumen, such as a blood vessel.

BACKGROUND

Many patients suffer from occluded arteries and other blood vessels which restrict blood flow. Occlusions can be partial occlusions that reduce blood flow through the occluded portion of a blood vessel or total occlusions (e.g., chronic total occlusions) that substantially block blood flow through the occluded blood vessel. In some cases a stent may be placed in the area of a treated occlusion. However, restenosis may occur in the stent, further occluding the vessel and restricting blood flow. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. A need remains for alternative atherectomy devices to facilitate crossing an occlusion.

SUMMARY

This disclosure provides design, material, manufacturing method, and use alternatives for medical devices. For example, the disclosure is directed to an atherectomy system that includes a handle having a handle housing with a drive motor disposed within the handle housing and adapted to rotate a drive cable extending through the handle and operably coupled to an atherectomy burr. A supply line extends from the handle housing. A supply line fitment is disposed relative to the handle housing and is configured to releasably secure the supply line relative to the handle housing such that the supply line is directed away from the handle housing in a direction that is selected from two or more directions.

Alternatively or additionally, the supply line may include a power line.

Alternatively or additionally, the supply line may include a saline line.

Alternatively or additionally, the supply line may include a tubular member with a power line and a saline line running through the tubular member.

Alternatively or additionally, the supply line may exit the handle from a position spaced apart from the supply line fitment.

Alternatively or additionally, the supply line may exit the handle from a position proximate the supply line fitment.

Alternatively or additionally, the supply line may exit the handle through the supply line fitment.

Alternatively or additionally, the supply line fitment may include two or more grooves formed within the handle housing, where the two or more grooves extend in different directions from where the supply line exits the handle housing.

Alternatively or additionally, the supply line fitment may include a rotatable knob secured relative to a proximal end of the handle housing, the rotatable knob including a graspable portion that may be rotated relative to the handle housing and a hollow protrusion extending from the graspable portion, the supply line passing through the hollow protrusion.

Alternatively or additionally, the supply line fitment may include a member pivotably coupled to the handle housing at a proximal end of the member, the member including a securement for releasably securing the supply line, the securement secured relative to a distal end of the member.

As another example, the disclosure is directed to an atherectomy system that includes a handle having a handle housing with a proximal end. A drive motor is disposed within the handle housing and is adapted to rotate a drive cable extending through the handle and operably coupled to an atherectomy burr. A rotatable knob is secured relative to the proximal end of the handle housing, the rotatable knob including a graspable portion that may be rotated relative to the handle housing and a hollow protrusion extending from the graspable portion. A supply line extends through the hollow protrusion of the rotatable knob.

Alternatively or additionally, the rotatable knob may be configured to rotate to a rotational position determined by the supply line reacting to gravity.

Alternatively or additionally, the rotatable knob may be configured to rotate through a range of about 180 degrees.

Alternatively or additionally, the rotatable knob may include one or more detents that sub-divide the range of about 180 degrees.

Alternatively or additionally, the rotatable knob may be configured to rotate through a range of about 135 degrees.

Alternatively or additionally, the supply line may include a power line.

Alternatively or additionally, the supply line may include a saline line.

As another example, the disclosure is directed to an atherectomy system that includes a handle having a handle housing with a drive motor that is disposed within the handle housing and is adapted to rotate a drive cable extending through the handle and operably coupled to an atherectomy burr. A supply line extends from the handle housing. A recess is formed within the handle housing, the supply line exiting the handle housing via the recess. A first groove is formed within the handle housing and extends from the recess in a first direction and a second groove is formed within the handle housing and extends from the recess in a second direction different from the first direction. The supply line is configured to be releasably engaged within either the first groove or the second groove.

Alternatively or additionally, the supply line may include a power line.

Alternatively or additionally, the supply line may include a saline line.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 6 is a side view of a portion of an advancer handle including an illustrative supply line fitment that may be used with the illustrative atherectomy system of FIG. 1; and FIG. 7 is a side view of a portion of an advancer handle including an illustrative supply line fitment that may be used with the illustrative atherectomy system of FIG. 1.

Figure 1:
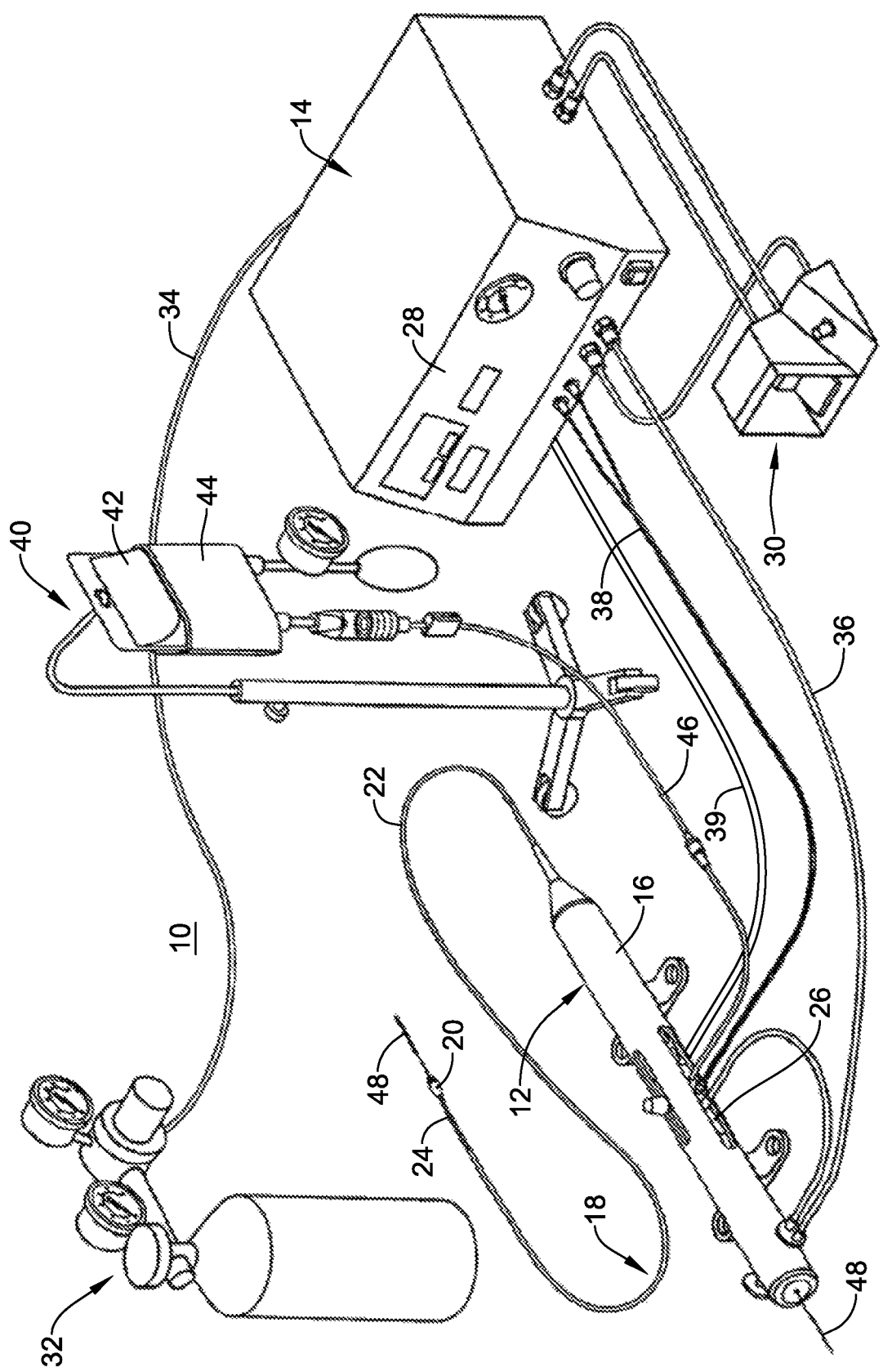
FIG. 1 is a schematic diagram of an illustrative atherectomy system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Many patients suffer from occluded arteries, other blood vessels, and/or occluded ducts or other body lumens which may restrict bodily fluid (e.g. blood, bile, etc.) flow. Occlusions can be partial occlusions that reduce blood flow through the occluded portion of a blood vessel or total occlusions (e.g., chronic total occlusions) that substantially block blood flow through the occluded blood vessel. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. Ideally, the cutting element excises the occlusion without damaging the surrounding vessel wall and/or a previously implanted stent where restenosis has occurred. However, in some instances the cutting element may be manipulated and/or advanced such that it contacts the vessel wall and/or the stent. Therefore, it may be desirable to utilize materials and/or design an atherectomy device that can excise an occlusion without damaging the surrounding vessel and/or a previously implanted stent where restenosis has occurred. Additionally, it may be desirable that a cutting element be useful in removing hard occlusive material, such as calcified material, as well as softer occlusive material. The methods and systems disclosed herein may be designed to overcome at least some of the limitations of previous atherectomy devices while effectively excising occlusive material. For example, some of the devices and methods disclosed herein may include cutting elements with unique cutting surface geometries and/or designs.

FIG. 1 shows an example rotational atherectomy system 10. The rotational atherectomy system 10 may include a rotational atherectomy device 12 and a controller 14 for controlling the rotational atherectomy device 12. The rotational atherectomy device 12 may include a housing 16 and an elongate shaft 18 extending distally from the housing 16 to a cutting member 20 located at a distal end of the elongate shaft 18. The elongate shaft 18 may include a drive shaft 24 to provide rotational motion to the cutting member 20. In some instances, the elongate shaft 18 may include an outer tubular member 22 having a lumen extending therethrough and the drive shaft 24 may extend through the lumen of the outer tubular member 22. The drive shaft 24, which may be fixed to the cutting member 20, may be rotatable relative to the outer tubular member 22 to rotate the cutting member 20. In some instances the axial position of the cutting member 20 relative to the outer tubular member 22 may be adjusted by moving the drive shaft 24 longitudinally relative to the outer tubular member 22. For example, the atherectomy device 12 may include an advancer assembly 26 positioned in the housing 16, or otherwise provided with the housing 16, that is longitudinally movable relative to the housing 16. The outer tubular member 22 may be coupled to the housing 16 while the drive shaft 24 may be coupled to the advancer assembly 26. Accordingly, the drive shaft 24 (and thus the cutting member 20) may be longitudinally movable relative to the outer tubular member 22 by actuating the advancer assembly 26 relative to the housing 16.

The rotational atherectomy device 52 may include a prime mover (not shown) to provide rotational motion to the drive shaft 24 to rotate the cutting member 20. For example, in some instances the prime mover may be a fluid turbine within the housing 16, such as provided with the advancer assembly 26. In other instances, however, the prime mover may be an electrical motor, or the like. The controller 14 may be used to control the prime mover. For example, the user may provide power to the prime mover and/or control the speed of rotation of the drive shaft 24 via the controller 14. For example, the front panel 28 of the controller 14 may include a user interface including a power switch, speed control mechanism (e.g., a speed control knob and/or buttons), a display, and/or other features for controlling the rotational atherectomy device 12. In some instances, the rotational atherectomy system 10 may include a remote control device 30, such as a foot pedal, a hand control, or other mechanism which may be used to control the power and/or speed to the prime mover, for example.

In instances in which the prime mover is an electric motor, the electric motor may be coupled to the controller 14 via an electrical connection 39 to control the electric motor and/or provide electricity to the electric motor.

In some instances, the rotational atherectomy device 12 may include a speed sensor, such as an optical speed sensor, coupled to the controller 14 via a connector 38, such as a fiber optic connector to provide speed data to the controller 14. In other instances, an electronic sensor, such as a Hall Effect sensor, or other type of sensor may be used to sense the speed of the drive shaft 24 and cutting member 20. The speed data may be displayed, such as on the front panel 28 and/or the controller 14, and/or used to control the speed of the cutting member 20, such as maintaining a desired speed of the cutting member 20 during a medical procedure.

In some instances, the rotational atherectomy system 10 may be configured to infuse fluid through the elongate shaft 18 to the treatment site and/or aspirate fluid through the elongate shaft 18 from the treatment site. In some cases, the rotational atherectomy system 10 may include a vacuum line 36 for aspiration purposes. For example, the rotational atherectomy system 10 may include a fluid supply 40 for providing a flow of fluid through a lumen of the elongate shaft 18 to a treatment site. In some instances the fluid supply 40 may include a saline bag 42 which may be pressurized by a pressure cuff 44 to provide a pressurized fluid (e.g., saline) to the rotational atherectomy device 12 through a fluid supply line 46. In other instances, an infusion pump, such as a peristaltic pump, may be used to deliver pressurized fluid to the rotational atherectomy device 12. Additionally or alternatively, in some cases the rotational atherectomy system 10 may be configured to aspirate fluid from the treatment site. For example, the rotational atherectomy system 10 may include an aspiration pump, such as a peristaltic pump, to generate a vacuum to aspirate fluid through a lumen of the elongate shaft 18 to a fluid collection container (not shown), if desired.

In some instances, the elongate shaft 18 of the rotational atherectomy device 12 may be advanced over a guidewire 48 to a treatment site. For example, the drive shaft 24 may include a guidewire lumen through which the guidewire 48 may pass. Additionally or alternatively, the elongate shaft 18 may be advanced through a lumen of a guide catheter to a treatment site.

Figure 2:
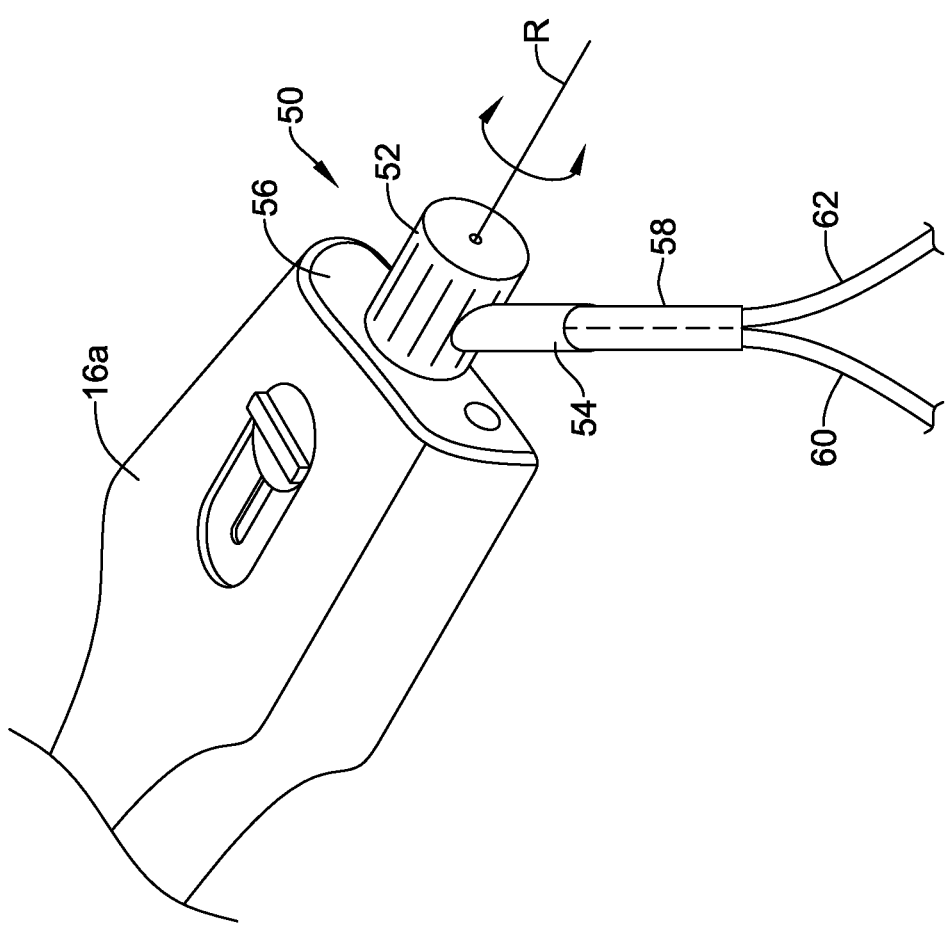
FIG. 2 is a perspective view of a portion of an advancer handle including an illustrative supply line fitment that may be used with the illustrative atherectomy system of FIG. 1.
Figure 3:
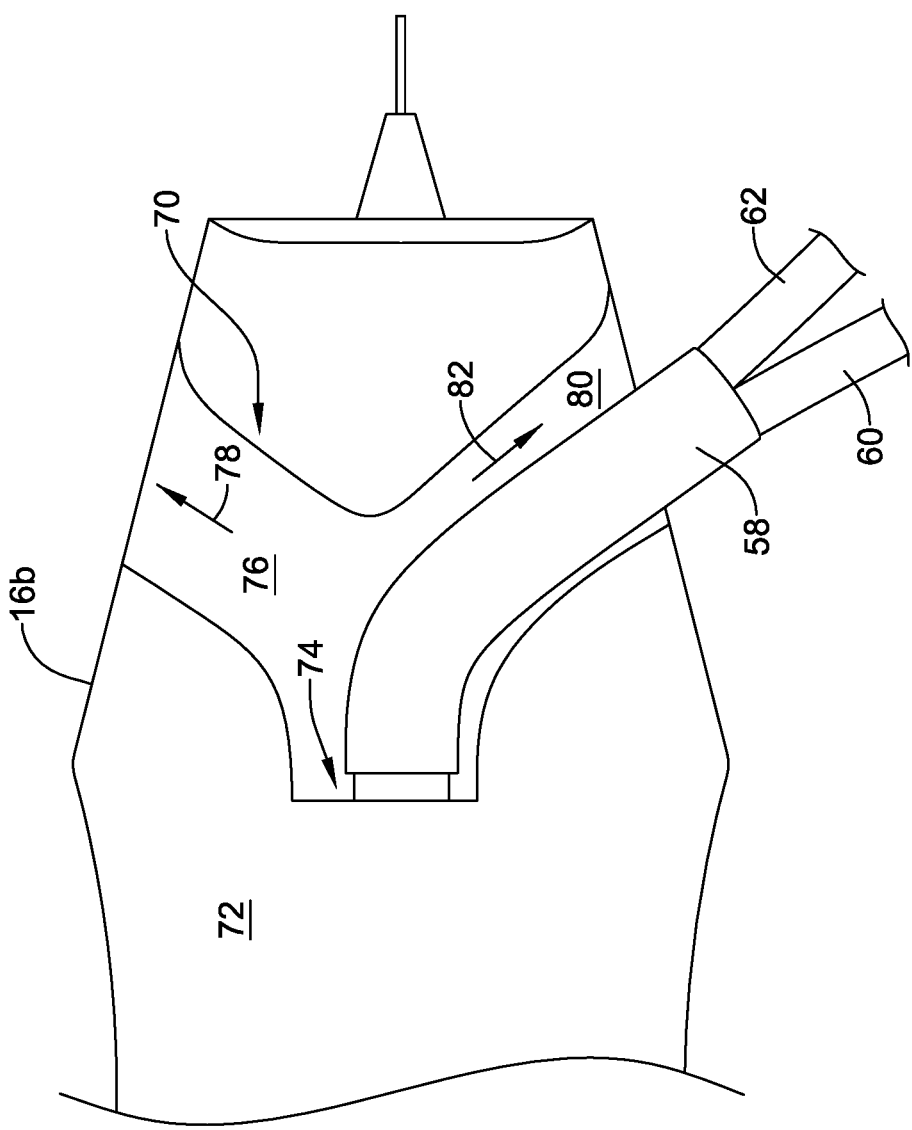
FIG. 3 is a side view of a portion of an advancer handle including an illustrative supply line fitment that may be used with the illustrative atherectomy system of FIG. 1.
Figure 4:
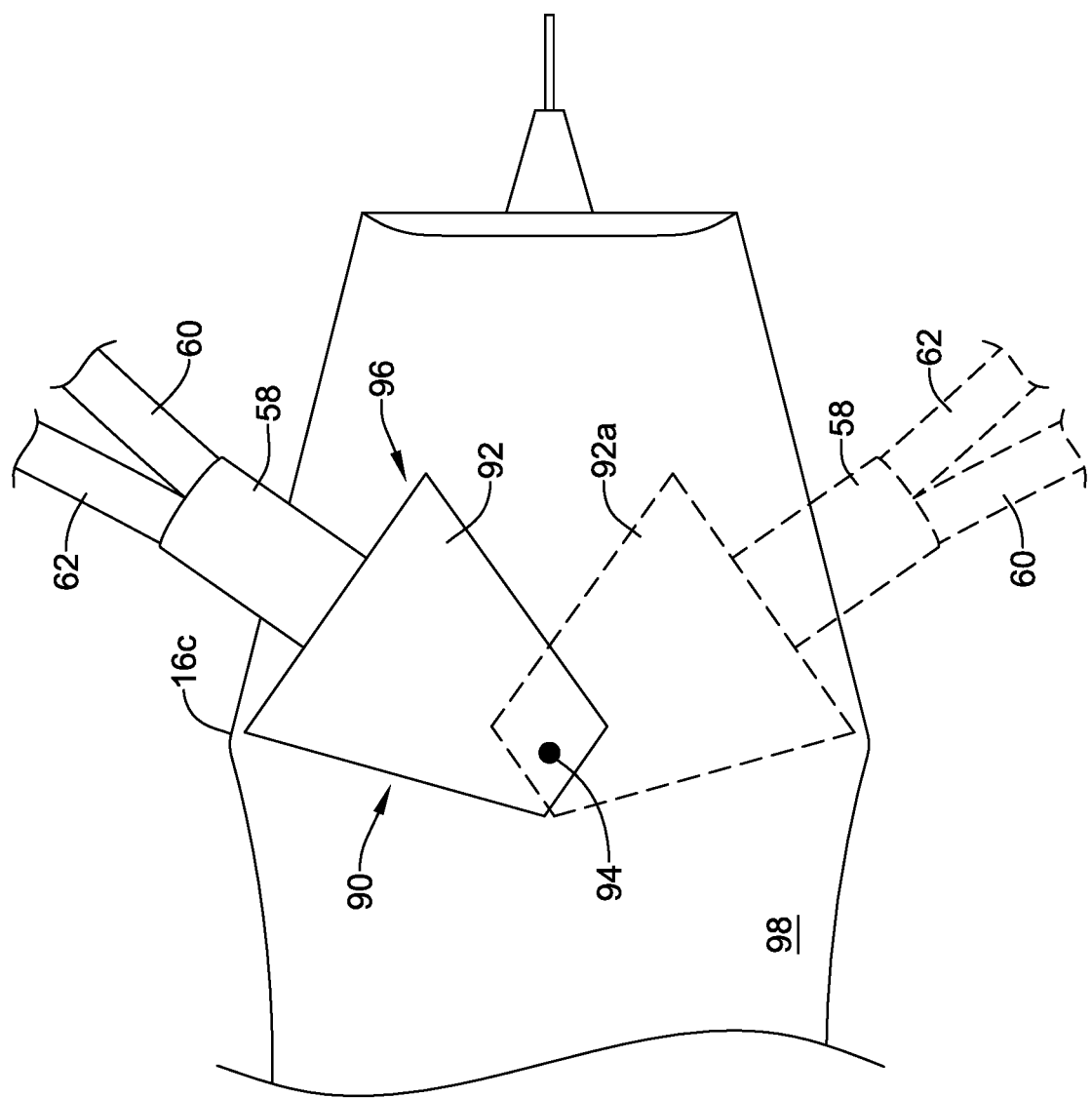
FIG. 4 is a side view of a portion of an advancer handle including an illustrative supply line fitment that may be used with the illustrative atherectomy system of FIG. 1.

As will be appreciated, there are potentially a number of different lines that are used in combination with the rotational atherectomy system 10, such as but not limited to a vacuum line 36, fiber optic lines 38, power lines 39 and a fluid supply line 46. Additional lines are contemplated. In some cases, there may be a desire to control the direction in which one or more of these lines exit the housing 16. FIGS. 2, 3 and 4 provide examples of additions and/or modifications that may be made to the housing 16 in order to provide control over the direction in which one or more of these lines exit the housing 16. Depending on the particular arrangement of a procedure room, catheterization room, operating room and the like, it may be helpful to be able to direct particular lines in a particular direction. In some cases, the housing 16 may be modified to include a supply line fitment that may be used to help direct a particular line in a particular direction. A supply line fitment may be added to an exterior of the housing 16. In some cases, for example, a supply line fitment may be attached to the exterior of the housing 16, or may be molded into the exterior of the housing 16.

FIG. 2 is a perspective view of a proximal portion of a housing 16*a*, in which the housing 16 shown in FIG. 1 has been modified by inclusion of a supply line fitment 50. It is considered that the supply line fitment 50 may be utilized with the housing 16. In some cases, as shown, the supply line fitment 50 may include a rotatable knob 52 and a hollow protrusion 54 that extends from the rotatable knob 52. It will be appreciated that the rotatable knob 52 may be rotated about an axis of rotation R that extends through the rotatable knob 52. As illustrated, the supply line fitment 50 extends proximally from a proximal end 56 of the housing 16*a*. The supply line fitment 50 may be secured to other portions of the housing 16*a*, if desired. As shown, a tubular member 58 extends through the hollow protrusion 54, with a first supply line 60 and a second supply line 62 passing through the tubular member 58. In some cases, the tubular member 58 may not be a tubular member, and may instead simply be tape that is used to secure together a portion of the first supply line 60 and the second supply line 62. The first supply line 60 and the second supply line 62 may each represent one of the supply lines discussed with respect to FIG. 1, including but not limited to the vacuum line 36, the fiber optic line 38, the power line 39 and the fluid supply line 46.

It will be appreciated that in some cases, the weight of the first supply line 60 and/or the second supply line 62 may cause the rotatable knob 52 to rotate until the first supply line 60 and/or the second supply line 62 reaches a stable position and is no longer moving in response to gravity. In some cases, for example, the first supply line 60 and/or the second supply line 62 may rest on a table top, or may simply hang in space. In some cases, the rotatable knob 52 may have a limited range of rotation, in order to not damage the tubular member 58 and/or the first supply line 60 and the second supply line 62. For example, in some cases the rotatable knob 52 may be configured to have a range of rotation that is greater than about 180 degrees. The rotatable knob 52 may be configured to have a range of rotation of about 180 degrees. The rotatable knob 52 may be configured to have a range of rotation of about 135 degrees. The rotatable knob 52 may, for example, be configured to have a range of rotation of about 90 degrees. These are just examples. In some cases, the rotatable knob 52 may rotate freely through its range of rotation. In some instances, the rotatable knob 52 may be configured to have one or more detents that provide an easy way for a user to locate one or more predetermined angles. For example, if the rotatable knob 52 has a range of rotation of about 180 degrees, the rotatable knob 52 may be configured to have detents at 45 degrees, 90 degrees and 135 degrees. In some cases, the supply lines 60, 62 may have an additional length within the handle 16*a* in order to accommodate rotation of the rotatable knob 52.

It will be appreciated, then, that the supply line fitment 50 enables a user to select a particular direction for the supply lines 60, 62 to extend from the housing 16*a*. Accordingly, the user is able to place the handle 16*a* in a location and orientation that is appropriate for the patient while also better accommodating the physical layout of the procedure room, and the location of particular equipment within the procedure room. For example, if one of the supply lines 60, 62 is a saline line, the user is able to better accommodate a particular location of a saline supply in the procedure room. If one of the supply lines 60, 62 is a power line, the user is able to better accommodate a particular location of a power supply within the procedure room.

FIG. 3 is a side view of a proximal portion of a housing 16b, in which the housing 16 shown in FIG. 1 has been modified by inclusion of a supply line fitment 70. In some cases, as shown, the housing 16b has an outer surface 72, and the supply line fitment 70 is formed within the outer surface 72. The supply line fitment 70 may be molded into the outer surface 72, for example. In some instances, the supply line fitment 70 may instead be cut into the outer surface 72. The supply line fitment 70 includes a recess 74 where the tubular member 58 (or an individual supply line 60, 62 if used individually) exits the housing 16b. The supply line fitment 70 includes a first groove 76 that is formed within the housing 16b and that extends from the recess 74 in a first direction that is indicated by an arrow 78. The supply line fitment 70 also includes a second groove 80 that is formed within the housing 16b and that extends from the recess 74 in a second direction that is indicated by an arrow 82. While a total of two grooves 76, 80 are shown, it will be appreciated that in some cases the supply line fitment 70 may include three or more distinct grooves, each extending in a different direction in order to accommodate additional directional options.

In some cases, the supply line fitment 70 may be formed on a lower surface of the housing 16b. In some instances, the supply line fitment 70 may instead be formed on a side or an upper surface of the housing 16b. Having the supply line fitment 70 in a particular location may be beneficial for use of the housing 16b in a particular rotational atherectomy system being used in a particular procedure room, for example.

FIG. 4 is a side view of a proximal portion of a housing 16c, in which the housing 16 shown in FIG. 1 has been modified by inclusion of a supply line fitment 90. The supply line fitment 90 includes a rotatable member 92 that pivots about a pivot 94. In some cases, the rotatable member 92 may be secured to the housing 16c via the pivot 94. The supply line fitment 90 also includes a securement 96 that may be used to releasably secure the tubular member 58 (or the supply lines 60, 62 individually) to the rotatable member 92. While the rotatable member 92 is shown as having a trapezoidal shape, in some cases the rotatable member 92 may have any of a variety of different shapes. The rotatable member 92 may have a triangular shape, a rounded shape or a rectilinear shape, for example.

FIG. 4 shows the supply line fitment 90 as being rotatable between a first position, as currently indicated by the illustrated position of the rotatable member 92, and a second position, where the rotatable member 92 is shown in dashed line and labeled as a rotatable member 92a. In some cases, the rotatable member 92 may pivot freely, within a plane of the paper, between the first position and the second position. In some instances, the weight of the tubular member 58 and/or the supply lines 60, 62 may cause the rotatable member 92 to rotate to a particular position and stabilize at that particular position. In some instances, the rotatable member 92 may move between two or more detents provided by an interaction between the rotatable member 92 and the pivot 94, or perhaps between the rotatable member 92 and an outer surface 98 of the housing 16c. For example, the outer surface 98 of the housing 16c may include one or more raised regions that are configured to interact with the rotatable member 92 and control movement of the rotatable member 92. In some cases, instead of pivoting about the pivot 94, the rotatable member 92 may instead be hingedly secured relative to the outer surface 98, and may pivot out of the plane of the paper. These are just examples.

Figure 5:
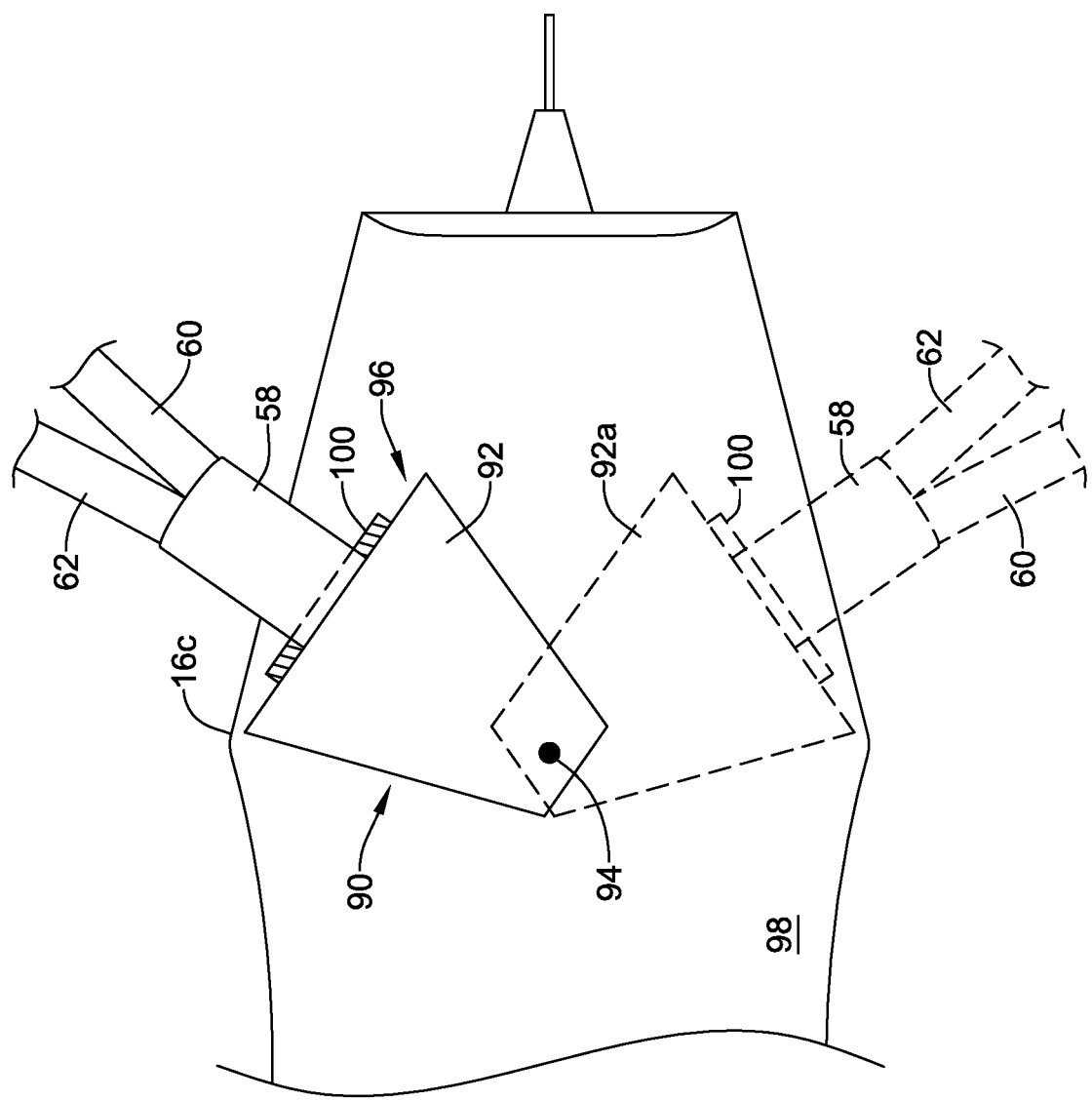
FIG. 5 is a side view of a portion of an advancer handle including an illustrative supply line fitment that may be used with the illustrative atherectomy system of FIG. 1.

The securement 96 may be any of a variety of different structures that are configured to releasably secure the tubular member 58 and/or the supply lines 60, 62 relative to the rotatable member 92. For example, FIG. 5 shows the securement 96 as being a raised clasp 100, secured relative to a lower surface of the rotatable member 92, that is configured to receive the tubular member 58 therein, and to frictionally engage an outer surface of the tubular member 58. In some cases, the securement 96 may include clips 102 and 104, as shown for example in FIG. 6. The clips 102 and 104 may be raised bumps or other features that are formed on an upper surface of the rotatable member 92, and may be spaced apart a distance that enables the tubular member 58 to be secured therebetween. FIG. 7 is similar, but employs a plurality of clips 102a, 102b, 102c along a first side of the tubular member 58 and a plurality of clips 104a, 104b, 104c along a second side of the tubular member 58. In some cases, the rotatable member 92 may include a plurality of securements 96, such that the supply lines 60 and 62 may be separately secured, without the tubular member 58. In some instances, the rotatable member 92 may include a plurality of securements 96, with each of the plurality of securements 96 configured for securing a different diameter supply line.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The scope of the disclosure is, of course, defined in the language in which the appended claims are expressed.

What is claimed is:

1. An atherectomy system, comprising:
a handle having a handle housing;
a drive motor disposed within the handle housing and adapted to rotate a drive cable extending through the handle and operably coupled to an atherectomy burr;
a supply line extending from the handle housing, the supply line comprising a tubular member with a power line and a saline line running through the tubular member;
a supply line fitment disposed relative to the handle housing, the supply line fitment configured to releasably secure the supply line relative to the handle housing such that the supply line is directed away from the handle housing in a direction that is selected from two or more directions.

2. The atherectomy system of claim 1, wherein the supply line exits the handle from a position spaced apart from the supply line fitment.

3. The atherectomy system of claim 1, wherein the supply line exits the handle from a position proximate the supply line fitment.

4. The atherectomy system of claim 1, wherein the supply line exits the handle through the supply line fitment.

5. The atherectomy system of claim 1, wherein the supply line fitment comprises a rotatable knob secured relative to a proximal end of the handle housing, the rotatable knob including a graspable portion that may be rotated relative to the handle housing and a hollow protrusion extending from the graspable portion, the supply line passing through the hollow protrusion.

6. The atherectomy system of claim 5, wherein the rotatable knob is configured to rotate to a rotational position determined by the supply line reacting to gravity.

7. The atherectomy system of claim 5, wherein the rotatable knob is configured to rotate through a range of about 180 degrees.

8. The atherectomy system of claim 7, wherein the rotatable knob includes one or more detents that sub-divide the range of about 180 degrees.

9. The atherectomy system of claim 5, wherein the rotatable knob is configured to rotate through a range of about 135 degrees.

10. The atherectomy system of claim 1, wherein the supply line fitment comprises a member pivotably coupled to the handle housing at a proximal end of the member, the member including a securement for releasably securing the supply line, the securement secured relative to a distal end of the member.

11. An atherectomy comprising:
a handle having a handle housing;
a drive motor disposed within the handle housing and adapted to rotate a drive cable extending through the handle and operably coupled to an atherectomy burr;
a supply line extending from the handle housing;
a supply line fitment disposed relative to the handle housing, the supply line fitment configured to releasably secure the supply line relative to the handle housing such that the supply line is directed away from the handle housing in a direction that is selected from two or more directions;
wherein the supply line fitment comprises two or more grooves formed within the handle housing, where the two or more grooves extend in different directions from where the supply line exits the handle housing.

12. The atherectomy system of claim 11, wherein the supply line comprises a power line.

13. The atherectomy system of claim 11, wherein the supply line comprises a saline line.

14. The atherectomy system of claim 11, wherein the supply line comprises a tubular member with a power line and a saline line running through the tubular member.

15. The atherectomy system of claim 11, wherein the supply line exits the handle from a position spaced apart from the supply line fitment.

16. An atherectomy system, comprising:
a handle having a handle housing;
a drive motor disposed within the handle housing and adapted to rotate a drive cable extending through the handle and operably coupled to an atherectomy burr;
a supply line extending from the handle housing;
a recess formed within the handle housing, the supply line exiting the handle housing via the recess;
a first groove formed within the handle housing and extending from the recess in a first direction; and
a second groove formed within the handle housing and extending from the recess in a second direction different from the first direction;
the supply line configured to be releasably engaged within either the first groove or the second groove.

17. The atherectomy system of claim 16, wherein the supply line comprises a power line.

18. The atherectomy system of claim 16, wherein the supply line comprises a saline line.

19. The atherectomy system of claim 16, wherein the supply line comprises a tubular member with a power line and a saline line running through the tubular member.

20. The atherectomy system of claim 16, wherein the supply line exits the handle from a position proximate the supply line fitment.

* * * * *